(12) United States Patent
Gerstner et al.

(10) Patent No.: US 7,292,332 B2
(45) Date of Patent: Nov. 6, 2007

(54) METHOD AND APPARATUS FOR DETECTING FAULTS IN TRANSPARENT MATERIAL

(75) Inventors: Klaus Gerstner, Mainz (DE); Clemens Ottermann, Hattersheim (DE); Thomas Zimmermann, Stukenbrock (DE); Josef Droste, Glandorf (DE)

(73) Assignees: Schott AG, Mainz (DE); Isra Vision Lasor GmbH, Oerling Hausen (DE)

( * ) Notice: Subject to any disclaimer, the term of this patent is extended or adjusted under 35 U.S.C. 154(b) by 273 days.

(21) Appl. No.: 10/812,161

(22) Filed: Mar. 29, 2004

(65) Prior Publication Data

US 2004/0207839 A1  Oct. 21, 2004

(30) Foreign Application Priority Data

Apr. 4, 2003  (DE) ................ 103 16 707

(51) Int. Cl.
   *G01N 21/00* (2006.01)

(52) U.S. Cl. .................................... 356/239.1

(58) Field of Classification Search .............. 356/239.1
   See application file for complete search history.

(56) References Cited

U.S. PATENT DOCUMENTS

| 4,492,477 | A | * | 1/1985 | Leser | ...................... 356/430 |
| 4,725,139 | A | * | 2/1988 | Hack et al. | ............... 356/237.1 |
| 4,808,813 | A | * | 2/1989 | Champetier | ................. 356/338 |
| 5,790,247 | A | * | 8/1998 | Henley et al. | ........... 356/237.1 |
| 6,151,125 | A | | 11/2000 | Mitsuhashi | |
| 6,346,713 | B1 | * | 2/2002 | Van Valkenburg | ..... 250/559.45 |
| 6,437,357 | B1 | | 8/2002 | Weiss et al. | |

FOREIGN PATENT DOCUMENTS

| DE | 201 21 763 U1 | 6/2003 |
| DE | 102 21 945 C1 | 7/2003 |
| WO | 99/49303 | 9/1999 |

OTHER PUBLICATIONS

Patent Abstracts of Japan, JP 10-339795, Published Dec. 22, 1998.

* cited by examiner

*Primary Examiner*—Tarifur Chowdhury
*Assistant Examiner*—Isiaka O Akanbi
(74) *Attorney, Agent, or Firm*—Michael J. Striker

(57) ABSTRACT

The method for detecting faults in transparent material includes irradiating a definite partial volume in the material with a first radiation source and coupling light into the material from a second source so that its optical path in the partial volume extends in the interior of the material. A fault in the partial volume is detected by light scattering, bright field absorption, and/or deflection of light of the first radiation source by the fault. The apparatus for detecting faults includes a first radiation source for illuminating a definite partial volume of the material, a detector for detecting light from this partial volume, and a second radiation source. The second radiation source is arranged in relation to the material so that the associated optical path in the partial volume passes exclusively in the interior of the material.

27 Claims, 5 Drawing Sheets

METHOD AND APPARATUS FOR DETECTING FAULTS IN TRANSPARENT MATERIAL

BACKGROUND OF THE INVENTION

1. The Field of the Invention

The present invention relates to a method and apparatus for detecting faults in transparent material. The purpose of the invention is to determine the optical quality and detect faults in the transparent material. The transparent material indeed is a solid material, especially glass or plastic. The plastic materials include, for example, polyvinyl chloride (PVC), polypropylene (PP), polyethylene (PE) or other transparent duroplastic or thermosetting plastic, elastomeric or thermoplastic materials. The use of the invention for determination of the quality of flat glass and float glass is especially preferred.

2. Description of the Related Art

WO 99/49303 describes a method and apparatus for detection of faults in flat glass. In this method a camera observes a spot on the boundary of a two-part lighting apparatus. The lighting apparatus is embodied in two parts with red LEDs in one half and with green LEDs in the other half. Relative motion between the camera and the lighting apparatus is detected. If a beam-deflecting fault is present in the flat glass, like, e.g., a sufficiently large bubble, this fault bends the beam guided to the camera from the lighting apparatus. Because of that different amounts of the red and green light reach the wavelength-sensitive camera so that a deflection signal is produced. In this way the apparatus can detect beam-deflecting faults. Furthermore the brightness field signal is used in order to measure the size of the corresponding beam-bending or beam-deflecting fault.

The Japanese Patent Publication H 10-339795 discloses detection of faults in flat glass by introducing parallel light beams inclined to side edges of the flat glass. Because of the way in which the light beams are introduced into the interior of the strip-shaped glass material total reflection occurs, so that the light travels from one side of the flat glass to the other. If a glass fault, for example an inclusion, a knot or a bubble, is present in the interior of the flat glass, the light introduced into the volume is scattered. The scattered light is detected in this method.

DE 102 21 945.1 of May 15, 2002 discloses a similar method, in which a laser light is introduced into a flat glass piece from the side or laterally. The laser light travels from one side of the flat glass to the other because of total reflection. In this method the laser beam is introduced at the side edge of the flat glass through water into the glass. Because of the manner in which the laser beam is introduced in this method the disadvantage that there is no definite edge geometry present in float glass is overcome. In this way this latter method differs from that disclosed in the aforementioned Japanese Patent Publication in which radiation is introduced laterally into the side edge only with difficulty in a definite manner and way.

SUMMARY OF THE INVENTION

It is an object of the present invention to provide a method for detecting faults in transparent material so that only signals from a certain partial volume of the transparent material are consulted for fault detection and fault size determination.

This object is attained by the invention claimed in the main independent claim. Additional advantages are attained by embodiments claimed in the appended dependent claims.

According to the invention the method for detecting faults in transparent material, comprises the steps of:

a) irradiating a definite partial volume of the transparent material with a first radiation source;

b) propagating light of a second radiation source into the transparent material so that an optical path of the light in the partial volume extends in an interior of the transparent material; and c) detecting scattered light from the fault in the partial volume, bright field absorption from the fault in the partial volume and/or deflection of light of the first radiation source by the fault in the partial volume to detect the presence of the fault in the partial volume.

In the context of the present invention the term "definite partial volume" of the transparent material means a localized region or part of the transparent material with definite boundaries, advantageously significantly smaller than the total volume of the transparent material.

A first embodiment of the method is based on the understanding that the prior art limitations regarding the usefulness of bright field methods for detecting faults in transparent material were due to a lack of spatial resolution of faults in these methods. Up to now it could not be determined whether a fault was in the bulk of the transparent material or on the surface of the material from the respective bright field signals whose strength is proportional to the local decrease in intensity of the bright field due to absorption. The bright field absorption can be caused by faults within the glass or also by faults, such as dirt, which are on the surface of the glass. The difference between these causes could not be determined by the bright field absorption methods according to the prior art.

Building on this understanding the basic concept of the invention is that the bright field methods are combined with a second method, which can be sensitive only to faults in certain volumes within the transparent material. Care is taken that only the same partial volume of transparent material is tested by both methods, so that it is guaranteed that both methods can detect the same fault. By combinations of both methods it is possible to test the coincidence of the bright field signal and the signal of the second method and to be able to express in the case of coincidence that the cause of the bright field signal is in the interior of the material. Without coincidence the fault is not in the volume measured, but on the surface. Thus in this latter case it would be a matter of a dirt effect in most cases.

Based on the above-described considerations one embodiment of the method of detecting faults in transparent material, which solves the above-described technical problems, comprises subjecting a definite partial volume of the transparent material to a bright field illumination with a first radiation source and coupling light into the transparent material with a second radiation source, so that the optical path in the partial volume extends exclusively in the transparent material. In this embodiment of the method a fault is detected in the partial volume when an absorption indicating such a fault is detected in the bright field and light of the second radiation source scattered by the fault is detected.

The signals produced by light scattering subsequently are designated the scattered light signal.

The second embodiment of the method according to the invention is based on the knowledge that prior art radiation deflection or bending methods for detecting faults in transparent material in which the transparent material is irradiated from the outside and the fault deflects or bends light acting on it similarly cannot differentiate between scattering centers or sites in the interior of the material or on the surface of the material.

Referring to the disclosure in the foregoing paragraphs the basic concept of the invention is to combine a radiation deflection or bending method with a second method, which responds exclusively to fault in the interior of the material, in other words in the bulk or volume of the material.

Based on this further inventive concept a further embodiment of the method for detecting faults in a transparent material comprises irradiating a definite partial volume with a first radiation source and introducing or coupling light into the material with a second radiation source so that the optical path that passes through the aforesaid partial volume is exclusively in the interior of the material. In this embodiment a fault is detected in the partial volume by detecting both scattered light from it and also deflection or bending produced by the light from the first radiation source.

The signals produced from the deflected light are designated in the following as the deflection signals.

Both of the above-described embodiments of the method can be performed alternatively or cumulatively. It is additionally possible in a third embodiment of the method of the invention to detect scattered light from the fault and the deflection of the light from the first radiation source produced by a fault in the partial volume, whereby radiation deflecting faults are tested in the material interior.

In summary, the solution of the above-described technical problems results in a method for detecting faults in transparent material, in which a definite partial volume of material is irradiated with a first radiation source and in which light is coupled into the material with a second radiation source so that the optical path in the aforesaid partial volume exclusively passes through the interior of the material. In this method a fault is determined to be present when light scattered from the fault, absorption in a bright field produced by the fault and/or deflection of light from the first radiation source produced by the fault is/are detected.

The apparatus solving the aforesaid technical problems and performing the method for detecting faults in transparent material according to the invention comprises a first radiation source for irradiating a definite and/or predetermined partial volume of the transparent material, a detector for detecting the light present in the above-described partial volume and a second radiation source, which is arranged in relation to the material, so that the optical path of light from the second radiation source passes exclusively through the interior of the material.

With reference to these embodiments a fault in the partial volume is detected from:

a) scattered light of the second radiation source scattered from the fault, and/or b) bright field light with an absorption produced by the fault, wherein the absorbed light is light from the first radiation source; and/or c) light of the first radiation source that was deflected by the fault.

A detector is arranged for the light of the second radiation source, which is scattered at the fault or defect in the material. This can be identical with the detector, which detects the light of the first radiation source or it can be different.

In a preferred embodiment the bright field light is measured with local spatial resolution. In this case the size of the fault or defect located in the partial volume may be determined. This is of great importance in the quality control in glass manufacture. Increasingly only small defects are permitted for high quality products. Thus for example prevention of defects with a diameter of greater than 50 µm is increasingly required in manufacture of TFT glass, which is used for flat display screens. In manufacture only a certain defined number of defects with a defect diameter of greater than 50 µm can be permitted. Whether the manufactured product meets these specifications can be concluded by the number of coincidence signals.

The type of fault can be deduced from the ratio of the bright field signal to the scattered light signal. If e.g. a bubble in the volume is illuminated by the method according to the invention, light is scattered in the part of the bubble on the side of the bubble from which radiation passes out. In contrast in the case of an inclusion scattering occurs on one side of the inclusion and comparatively little total scattered light is produced for an inclusion of the same size. Thus whether or not the fault is a bubble or an inclusion can be determined from the aforesaid signal ratio. Also the type of fault can be determined from the ratio of the deflection signal to the scattered light signal. Additional faults in the transparent material may be generally considered. In further testing according to the invention each fault type has its own characteristic three-dimensional radiation pattern, so that the type of the detected fault can be established from these characteristic radiation patterns.

In particularly advantageous embodiments the second radiation source emits monochromatic light, i.e. is a laser. In this embodiment monochromatic light from this second radiation source is especially easily introduced or coupled into a flat glass sheet through a side edge. Furthermore this has the advantage that a high light intensity is available. With a flat glass, which for example is illuminated with a halogen lamp, that the intensity of the input light strongly decreases in the center of the sheet because of absorption, for example to 5% of the input value with a 1.2-m sheet, should be considered. In this latter case an expensive computer compensation is required in an evaluation in order to correctly judge the size of the fault over the total width of the sheet from the scattered light. However a laser has the potential that sufficient intensity is present along the laser beam in this embodiment of the method according to the invention.

An advantageous application of the method according to the invention includes coupling the respective radiation into a flat glass sheet and testing it according to the fault. This flat glass is moving with respect to the radiation sources under production conditions, indeed at a feed speed of 10 m/min, so that about 26 m$^2$ per minute can be tested based on the width of the flat glass plate. The thickness of this sort of glass typically is between 0.4 and 1.1 mm.

When the second radiation source emits green light or light in the green range, the absorption effects are particularly small in technical glass. This glass has iron-containing impurities with an absorption minimum in this green wavelength range. Accordingly it is advantageous when the emission frequency of the laser selected is 532 nm.

When the second radiation source emits red light, absorption effects are especially small in optical glasses. In this case a helium-neon laser or LEDs emitting in the red wavelength range or diode lasers are available as radiation sources. It is generally advantageous to select the wavelength of the radiation sources so that as little radiation as possible is absorbed.

In experiments it has been shown that it is advantageous when the intensity of the light coupled into the material edge by the second radiation source is about 10 times as high, as in the center. In experiments with light coupled into flat glass it was established that simply increasing the intensity of the input light is no solution for compensating the weakening of the light intensity with the not eliminated absorption occurring in the glass. Furthermore noise signals, which are probably caused by dirt on the glass surface, are produced. In so far as dirt on the surface is illuminated difficulties are produced for the signal processing. The above-described intensity ratio produces a good balance between sufficiently high intensity and sufficiently small noise signals. In order to adjust this intensity ratio the wavelength can be adjusted for the respective material, since the absorption experiences material-dependent changes at different wavelengths. Alternatively or cumulatively the intensity ratio can be provided also by a changed focussing of the input laser light.

In order to guarantee that the light of the second radiation source in the partial volume being tested travels exclusively within the interior of the material, the light of the second radiation source can be input in such a way that it is totally reflected in the interior. This can be provided by introducing the light inclined to the upper side or lower side of the material and indeed so that the angle of incidence in relation to the surface normal is greater than the limiting or boundary angle for total reflection in subsequent transmission of light from the transparent material to air. Alternatively the light can also be input inclined to the side edge of the material. This pre-condition is especially suited for testing of flat glass or float glass, in which light so-to-speak is captured in the interior, as in an optical fiber. At the same time not only a small partial volume can be tested, but the flat glass can be tested over its entire width. Accordingly the associated apparatus must be designed so that it can probe not only a single small partial volume, but also a plurality of small partial volumes across the feed direction of the flat glass.

When float glass should be tested for faults with the method according to the invention and it has no definite edge geometry at its edges, the second radiation source can be used to input light inclined to the side edge. In so far as it is advantageous a transparent liquid, like water, can be arranged between the second radiation source and the float glass so that the light of the second radiation source is coupled into the sheet or strip of float glass through the transparent liquid. Because of the transparent liquid, which is in contact with the non-uniform edges, geometric differences are compensated and input of the laser light is possible.

When both radiation sources emit pulsed light, so that one radiation source emits light exclusively in intervals between pulses of the other radiation source, a single detector can be used for detection of the fault in the transparent material. Thus the bright field signal from the radiation of the first radiation source is detected temporally shifted from the corresponding scattered light signal. Detection of these signals alternate. Since, on the other hand, the testing depends on receiving signals from the same partial volume, it is understandable that the feed speed of the material must be adjusted to the suitable pulse duration of the radiation sources. In that way it is guaranteed that both radiation sources illuminate the same partial volumes. Accordingly electronics, generally a multiplexing unit, must be provided for controlling both radiation sources, which is constructed so that the radiation sources exclusively emit time-shifted light pulses.

The principal method according to the invention only registers a coincidence, when radiation absorption is established in bright field light. If this absorption is too small or it is not present at all, the corresponding fault is not found. In this latter case however it is possible to detect this fault by its radiation deflection action. If bright field illumination is performed in transmission, i.e. the transparent medium is located between camera and light source, the light acting on the fault is deflected in the case of a radiation-deflecting fault. The deflected light thus falls on the detector at a different position than undeflected light that has not experienced this deflecting effect.

In order to detect this sort of radiation deflection the first radiation source can be a two-part radiation source. Light of two different intensities or colors can be emitted from the respective parts of the radiation source. For example if two colors are emitted, e.g. red and green, the radiation deflecting action of a fault or defect changes the amount of red and green light reaching the detection. If respective voltage signals $U_1$ and $U_2$ at the detector are correlated with the corresponding colors, a change of these voltage signals $U_1$ and $U_2$ corresponds to a deflection of the radiation. The difference of both voltages is a measure for the amount of the deflection.

Alternatively the ratio $$U_{pos}=\{U_1-U_2\}/\{U_1+U_2\}$$

can be referred to, i.e. used to find a fault by this embodiment of the method. The amplitude of $U_{pos}$ is thus a measure of the amount of the deflection caused by the fault or defect.

By the additional detection of deflected radiation several types of faults are thus detected by measurement engineering techniques. The reliability of the detection of the faults with a maximum size, which is still acceptable in the manufacturing process, increases.

It is also possible to simultaneously work with the scattered light signal, the radiation deflection signal and the bright field signal. Radiation-deflecting sites on the surface can be detected in this way and ignored during the quality control testing of the material. In case these three signals simultaneously coincide or are positive, this indicates the presence of a radiation-deflecting and radiation-absorbing fault, which is in the interior or bulk of the material. The circumstance that this fault also deflects radiation permits an extensive and improved categorization of faults, as described above.

The generation of the different colored light by both parts of the first radiation source can occur when both parts comprise different LEDs that produce the different colored light. A CCD camera can then detect the light from this two-part source.

It is possible to detect the scattered light, on the one hand, and the deflected radiation and/or the bright field signal, on the other hand, with different detectors.

In order to keep the apparatus expense low it is advantageous when both radiation sources are pulsed so that the first radiation source is preferably a pulsed radiation source. In combination with a pulsed second radiation source, for example a pulsed laser, it can be guaranteed that one radiation source emits pulses exclusively in the interval between pulses from the other radiation source. For this purpose the apparatus has an electronic device controlling both radiation sources, which is formed so that both radiation sources exclusively emit time-shifted light.

If, as mentioned above, a two-part first radiation source is selected, this corresponds to embodiments with three light sources, in as much as the one light source emits in the intervals between the pulses of the both other light sources.

An analyzing or evaluating unit is also provided for processing the detected signals to ascertain the bright field signal, scattered light signal and/or deflection signal.

BRIEF DESCRIPTION OF THE SEVERAL VIEWS OF THE DRAWING

The objects, features and advantages of the invention will now be illustrated in more detail with the aid of the following description of the preferred embodiments, with reference to the accompanying figures in which.

DETAILED DESCRIPTION OF THE INVENTION

Figure 1:
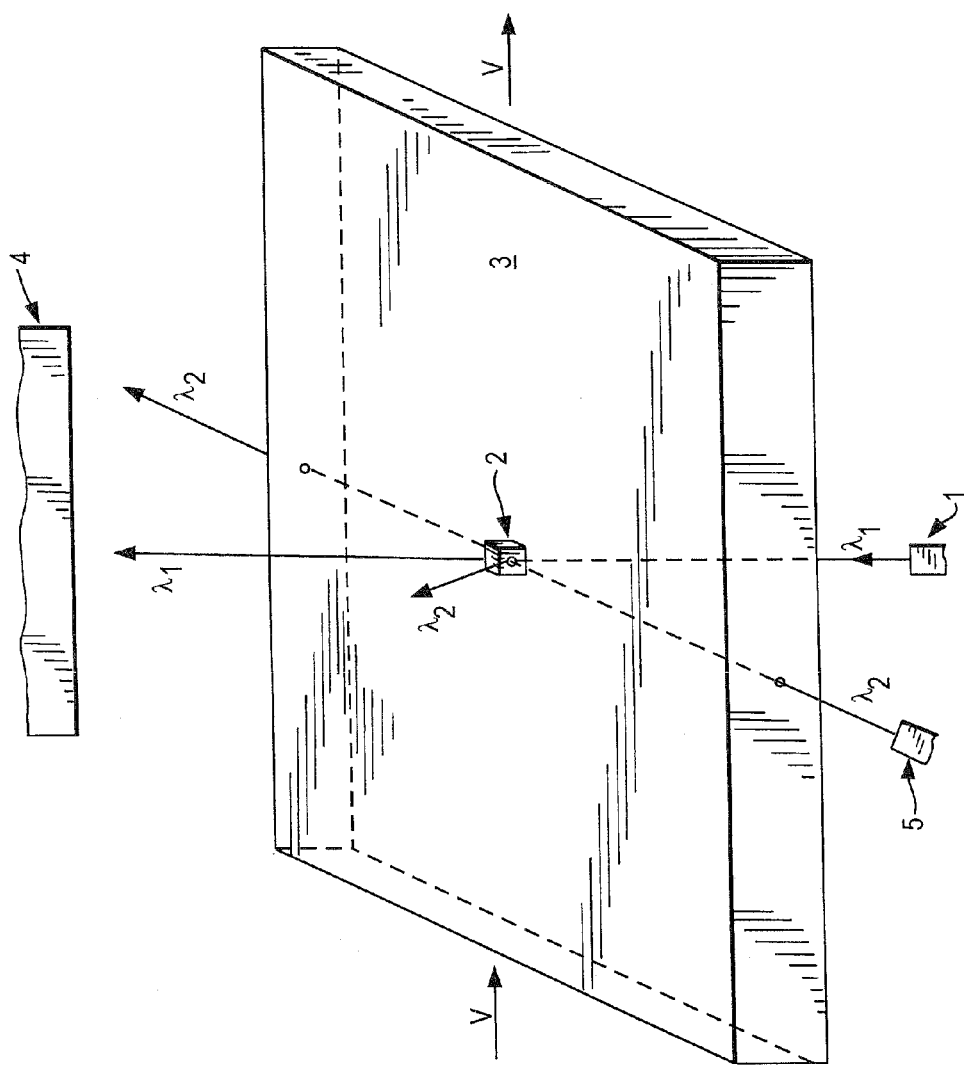
FIG. 1 is a perspective view illustrating a first embodiment of an apparatus for performing the method for detecting faults in a transparent material according to the invention.

FIG. 1 is a diagrammatic representation showing the method according to the invention, in which a first radiation source 1 with wavelength A, irradiates a plate-shaped glass body 3 from underneath it. After the light passes through it twice it reaches the detector 4. The radiation source 1 probes a partial volume 2 in the interior of the glass material 3.

The glass part 3 is irradiated laterally or from the side edge of the glass plate 3 by means of a second radiation source 5 with light of wavelength $\lambda_2$. The light from the second light source is partially scattered in the given partial volume 2, which is indicated by the arrow directed laterally toward the left in FIG. 1. The glass plate 3 moves laterally from left to right with speed v.

Figure 2:
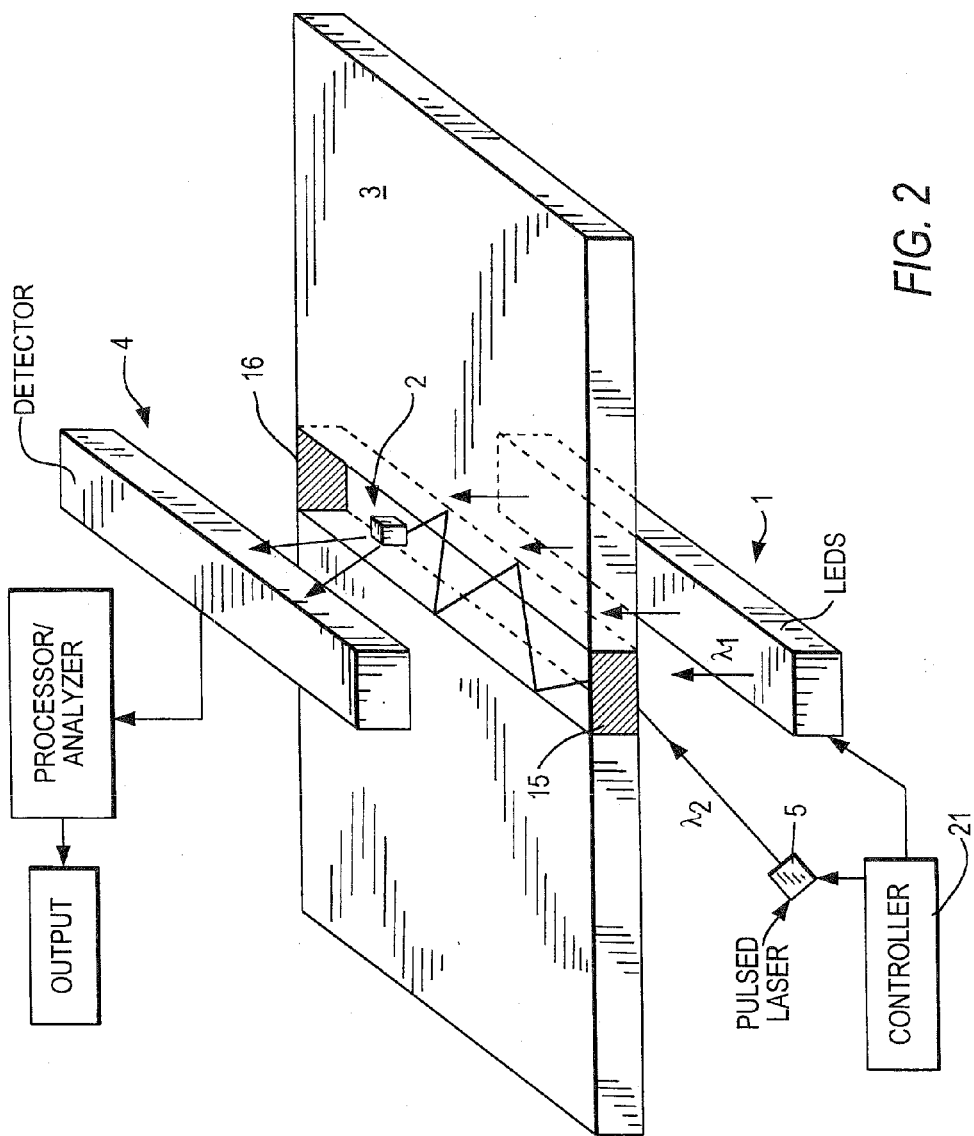
FIG. 2 is a perspective view of a second embodiment of an apparatus for performing the method for detecting faults in a transparent material according to the invention.

FIG. 2 shows the glass plate 3 again, this time with a bar-shaped light source 1 underneath it, which emits light of wavelength $\lambda_1$ perpendicularly to the under side or under surface of the plate. Also radiation of wavelength $\lambda_2$ reaches the region 15 through the side edge of the glass plate 3, as shown in FIG. 2, from the second radiation source 5. This light of wavelength $\lambda_2$ is coupled into the glass plate 3 so that it is totally reflected in the interior, which is indicated by the zig-zag line in the region 15. The totally reflected light is partially scattered in the partial volume 2 and the scattered light arrives in the detector 4. The fraction of the light of wavelength $\lambda_2$ that passes through the glass plate 3 without being scattered passes out of the surface 16 at the other end or side of the glass plate 3. An electronic device 21 for controlling the first and second radiation sources 1, 5 is provided in preferred embodiments in which the radiation sources are pulsed, so that it can be guaranteed that one radiation source emits pulses exclusively in the interval between pulses from the other radiation source. For example the second radiation source 5 can be a pulsed laser in some embodiments. In addition, an analyzing unit 23 for processing the detected signals from the detector 4 to obtain an output signal or similar output, which expresses the desired result of the method must be provided.

Figure 3:
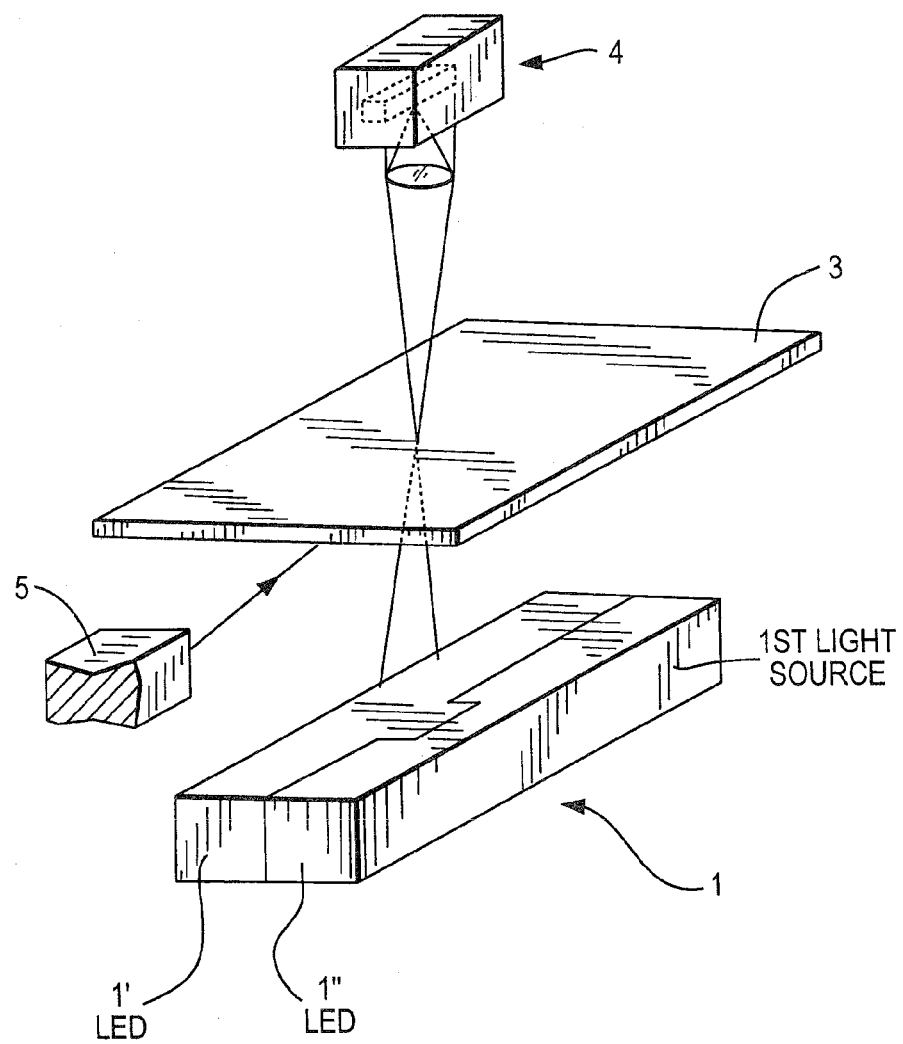
FIG. 3 is a perspective view of another embodiment of an apparatus for performing the method for detecting faults in a transparent material according to the invention, which is similar to the apparatus shown in FIG. 2.

FIG. 3 shows an apparatus that is similar to that shown in FIG. 2. The embodiment shown in FIG. 3 differs from that of FIG. 2 in that the bar-shaped light source 1 has two parts, a first part 1' and a second part 1". A CCD camera 4 focuses on the partial volume in the glass plate 3. Further in this direction the detector 4 detects a part of the surface of the bar-shaped light source 1 radiating pulsed light at the boundary between the parts 1' and 1".

Figure 4:
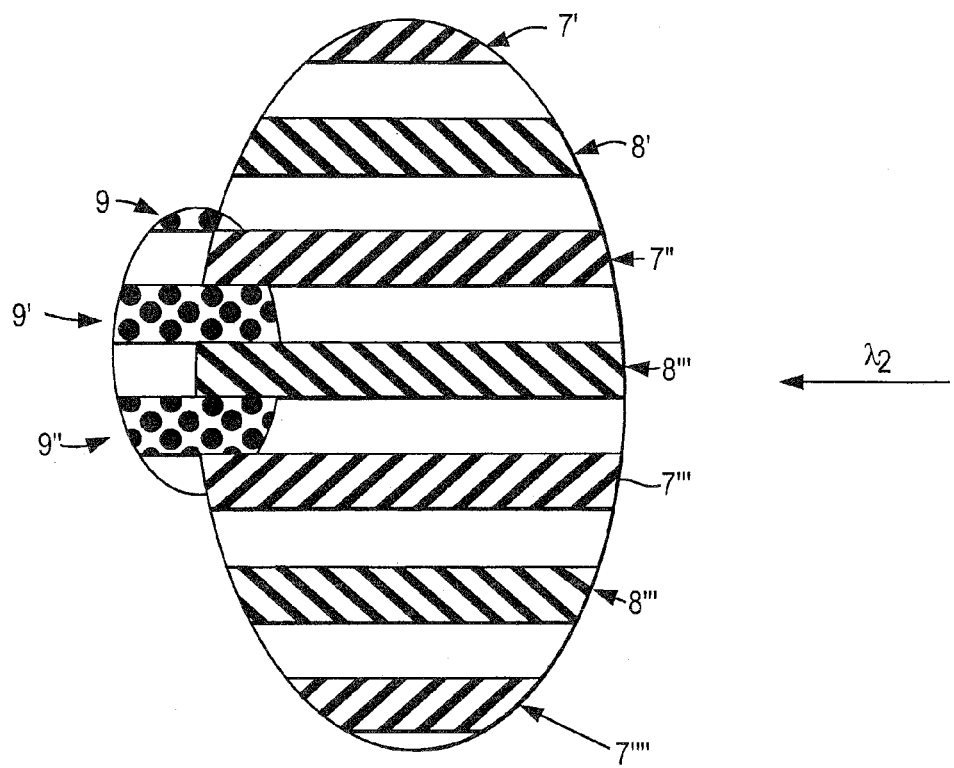
FIG. 4 is a diagrammatic illustration of a fault in a transparent material in the form of a bubble.

FIG. 4 is a diagrammatic representation of a known fault in the glass in the form of a bubble. The size and the approximately egg-shaped structure are obtained by evaluation of the bright field absorption. The CCD chip alternately detects the light LED 1 and the light LED 2, namely 7', 8', 7", 8", 7''', 8''', 7'''', 8''''. LED 1 stands for the light of the first part 1' of the light source 1 and LED 2 stands for the light of the second part 2".

Also light of wavelength $\lambda_2$ from the second radiation source 5 is coupled into the glass plate 3 through the edge laterally from left to right in FIG. 3. This edge light passes through the bubble (fault) from right to left, which leads to scattering in the irradiated region.

Figure 5:
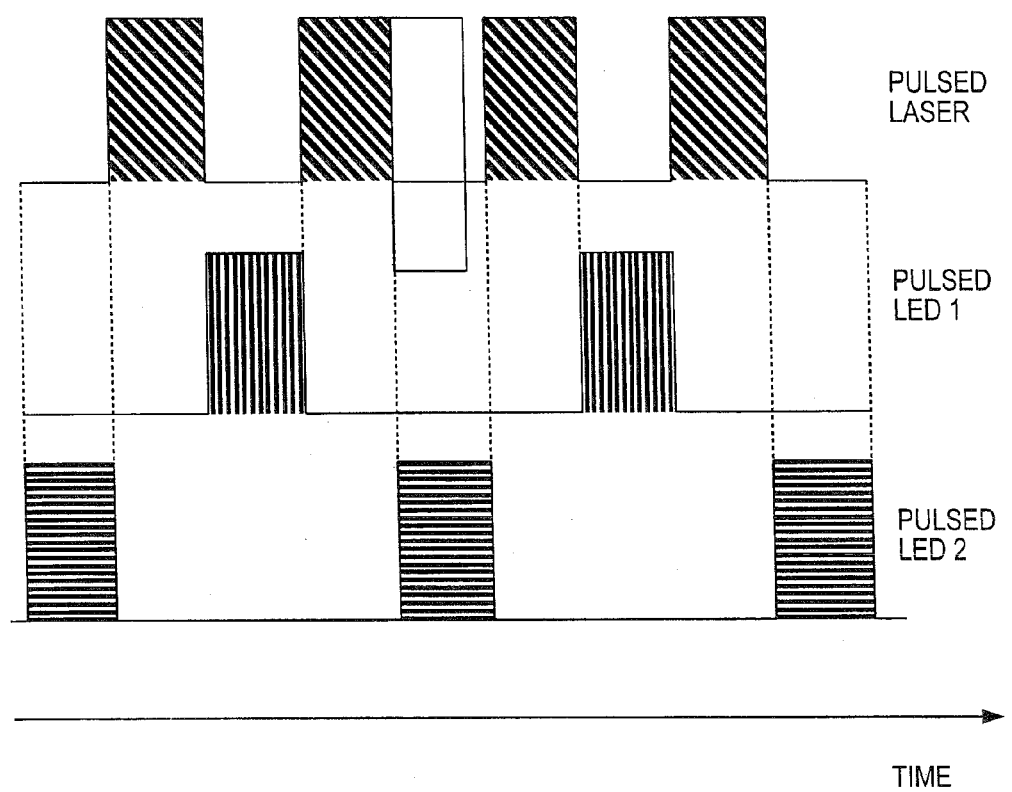
FIG. 5 is a pulse-timing diagram showing the temporal relationship of laser and LED pulses used in the method according to the invention.

The laser pulse from the second radiation source 5 is adjusted to the pulse timing of the parts 1' and 1" as shown in FIG. 5. The synchronization performed is shown in FIG. 5. Respective light pulses from the first part 1' and the second part 1" of the first radiation source are alternately emitted following individual laser light pulses of the second radiation source 5. The one light source thus emits a pulse in the common pause interval between the pulses from the other light source. The single detector detects in succession laser light 9' in the scattering region, light 7" of LED 1, laser light 9", light 8''' of LED 2, laser light 9''' and light 7''' from LED 1 as shown in FIG. 4.

The disclosure in German Patent Application 103 16 707.2 of Apr. 4, 2003 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method and apparatus for detecting faults in a transparent material, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method for detecting faults in a transparent manufactured material in order to ascertain whether or not the transparent manufactured material meets predetermined specifications during quality control testing, said method comprising the steps of:
   a) irradiating a definite partial volume entirely within an interior of the transparent manufactured material with a first radiation source;
   b) coupling light of a second radiation source into the transparent manufactured material so that an optical path of said light passes through said definite partial volume entirely within said interior of the transparent manufactured material;

c) detecting scattered light from said fault in said partial volume, detecting bright field absorption from said fault in said partial volume and/or detecting deflection of light of said first radiation source by said fault in said partial volume in order to detect the presence of said fault in said partial volume of the transparent manufactured material; and d) determining a fault type of said fault from a ratio of a bright field signal to a scattered light signal or from a ratio of a deflection signal to said scattered light signal; and e) producing an output signal characterizing the fault type of said fault detected within said definite partial volume according to said ratio.

2. The method as defined in claim 1, further comprising measuring the material with local spatial resolution.

3. The method as defined in claim 1, wherein said second radiation source emits monochromatic light.

4. The method as defined in claim 1, wherein said transparent manufactured material is a flat glass sheet or a flat glass plate.

5. The method as defined in claim 1, wherein said second radiation source emits green light.

6. The method as defined in claim 5, wherein said green light has a wavelength of 532 nm.

7. The method as defined in claim 1, wherein said second radiation source emits red light.

8. The method as defined in claim 1, wherein said light of the second radiation source coupled into the transparent manufactured material has an intensity that is about ten times higher at an edge of the transparent manufactured material than in a center of the transparent manufactured material.

9. The method as defined in claim 8, wherein said light of the second radiation source is coupled into the transparent manufactured material so that said light experiences total reflection in the interior of the transparent manufactured material.

10. The method as defined in claim 4, wherein said light of the second radiation source is coupled into the flat glass sheet or flat glass plate so that said light experiences total reflection in the interior of the transparent manufactured material.

11. The method as defined in claim 4, wherein said light of the second radiation source is coupled into the transparent manufactured material through a transparent liquid.

12. The method as defined in claim 1, wherein both of said radiation sources emit pulsed light and one of the radiation sources emits pulses of said pulsed light only in pause intervals between pulses from another of the radiation sources.

13. The method as defined in claim 1, wherein said first radiation source is divided into two parts and said two parts emit different colored light.

14. An apparatus for detecting faults in transparent material, said apparatus comprising
    a first radiation source for illumination of a definite partial volume of the transparent material,
    a detector for light originating from said partial volume; and
    a second radiation source arranged in relation to the transparent material so that an associated optical path extends exclusively in an interior of the transparent material;
    wherein said first radiation source comprises two parts emitting light of different intensities and wavelengths.

15. The apparatus as defined in claim 14, wherein said two parts of the first radiation source comprise different colored LEDs.

16. The apparatus as defined in claim 14, wherein said first radiation source is pulsed.

17. The apparatus as defined in claim 14, wherein said detector is arranged for detection of bright field tight in such a way that said detector detects radiation from both of said two parts of the first radiation source.

18. The apparatus as defined in claim 14, wherein one of said first radiation source and said second radiation source emits in a green wavelength range.

19. The apparatus as defined in claim 14, wherein said second radiation source is a laser.

20. The apparatus as defined in claim 19, wherein said laser has an emission frequency of 532 nm.

21. The apparatus as defined in claim 19, wherein said laser is a pulsed laser.

22. The apparatus as defined in claim 14, further comprising an electronic device for controlling said first radiation source and said second radiation source so that the first radiation source and the second radiation source emit only time-shifted light.

23. The apparatus as defined in claim 14, wherein said detector detects a bright field signal, a scattered light signal and/or a deflection signal.

24. The apparatus as defined in claim 14, wherein said detector is a CCD camera.

25. The apparatus as defined in claim 14, wherein said first radiation source composes two different light emitting diodes (LEDs) and said two different light emitting diodes emit light of different colors or intensities.

26. An apparatus for detecting faults in a transparent manufactured material to determine whether or not the transparent manufactured material meets specifications during quality control testing, said apparatus comprising
    a first pulsed light source arranged to illuminate a definite partial volume in an interior of the transparent manufactured material,
    a detector for light originating from said definite partial volume;
    a second pulsed light source arranged in relation to the transparent manufactured material so that an optical path of light from said second pulsed light source extends exclusively through the definite partial volume in the interior of the transparent manufactured material; and
    an electronic means for controlling said first pulsed light source and said second pulsed light source, so that said first pulsed light source emits light pulses exclusively in intervals between light pulses originating from said second pulsed light source wherein said first radiation source comprises two part emitting light of different intensities and wavelengths.

27. A method for detecting faults in a transparent manufactured material in order to ascertain whether or not the transparent manufactured material meets predetermined specifications during quality control testing, said method comprising the steps of;
    a) irradiating a definite partial volume entirely within an interior of the transparent manufactured material with a first radiation source;
    b) coupling light of a second radiation source into the transparent manufactured material so that an optical path of said light passes through said definite partial volume entirely within said interior of the transparent manufactured material;

c) detecting scattered light from said fault in said partial volume, detecting bright field absorption from said fault in said partial volume and/or detecting deflection of light of said first radiation source by said fault in said partial volume in order to detect the presence of said fault in said partial volume of the transparent manufactured material; and d) determining a fault type of said fault from a ratio of a bright field signal to a scattered light signal or from a ratio of a deflection signal to said scattered light signal;

e) providing an analyzing unit for processing detected signals from said definite partial volume, said detected signals including said scattered light signal and said detected signals also including said bright field signal and/or said deflection signal, in order to ascertain the type of said fault within said definite partial volume according to said ratio determined in step d); and f) outputting the type of said fault from said analyzing unit.

* * * * *